(12) United States Patent
Mayne et al.

(10) Patent No.: US 6,881,427 B2
(45) Date of Patent: Apr. 19, 2005

(54) TOPICAL ANTI-INFLAMMATORY COMPOSITION CONTAINING LINSEED AND LICORICE EXTRACTS

(75) Inventors: James R. Mayne, Kentwood, MI (US); Haeri Roh-Schmidt, Ada, MI (US)

(73) Assignee: Alticor Inc., Ada, MI (US)

( * ) Notice: Subject to any disclaimer, the term of this patent is extended or adjusted under 35 U.S.C. 154(b) by 129 days.

(21) Appl. No.: 10/061,998

(22) Filed: Jan. 31, 2002

(65) Prior Publication Data

US 2003/0143288 A1 Jul. 31, 2003

(51) Int. Cl.⁷ .............................................. A61K 35/78
(52) U.S. Cl. ...................................... 424/757; 424/768
(58) Field of Search .................. 424/757, 768, 424/725

(56) References Cited

U.S. PATENT DOCUMENTS

| | | | |
|---|---|---|---|
| 4,481,185 A | | 11/1984 | Grollier et al. |
| 5,397,778 A | * | 3/1995 | Forse et al. ................. 514/198 |
| 5,560,910 A | | 10/1996 | Crandall |
| 5,767,095 A | | 6/1998 | Winget |
| 6,153,208 A | | 11/2000 | McAtee et al. |
| 6,174,533 B1 | | 1/2001 | SaNogueira, Jr. et al. |
| 6,184,247 B1 | | 2/2001 | Schneider |
| 6,190,678 B1 | | 2/2001 | Hasenoehrl et al. |

FOREIGN PATENT DOCUMENTS

| | | |
|---|---|---|
| EP | 0 992 236 A1 | 4/2000 |
| EP | 1 062 944 A1 | 12/2000 |
| JP | 393237 * | 10/1992 |
| JP | 2000-212060 | 8/2000 |
| JP | 2001-261570 | 9/2001 |
| WO | WO 98/05294 | 2/1998 |
| WO | WO 99/52502 | 10/1999 |
| WO | WO 01/02028 A2 | 1/2001 |

OTHER PUBLICATIONS

English Abstract No. XP–002239068 of RU 2145839 to N. V. Nazarova et al. published Feb. 27, 2000.
English Abstract No. XP–002239069 of 2000 212060 to Hiroshi Tanaka published Aug. 2, 2000.
English Abstract No. XP–002239072 of RU 2089178 to S. N. Belov published Sep. 10, 1997.
English Abstract No. XP–002239070 of JP 2001 261570 to Kumi Kameyama et al. published Sep. 26, 2001.
English Abstract No. XP–002239071 of JP 5194176 to Mieko Nishida et al. published Aug. 3, 1993.
English Abstract of JP 63280006 to Yakult Honsha Co. Ltd. Published Nov. 17, 1988.
PM O'Byrne, GM Gauvreau, and LJ Wood, "Anti–Inflammatory Agents In The Treatment Of Allergic Airway Disease", *World Equine Airways Symposium*, Aug. 4–8, 1998, pp. 1–6.
English Abstract of JP 5058902 A2, Mar. 9, 1993, 2 pages.

* cited by examiner

*Primary Examiner*—David M. Naff
*Assistant Examiner*—Deborah K. Ware
(74) *Attorney, Agent, or Firm*—Brinks Hofer Gilson & Lione; Gregory H. Zayia

(57) ABSTRACT

Topical anti-inflammatory compositions are described that include effective amounts of a linseed extract and a licorice extract. In addition, methods of reducing inflammation are described, which include applying topically to a site of inflammation an effective amount of a composition comprising a linseed extract and a licorice extract.

13 Claims, 3 Drawing Sheets

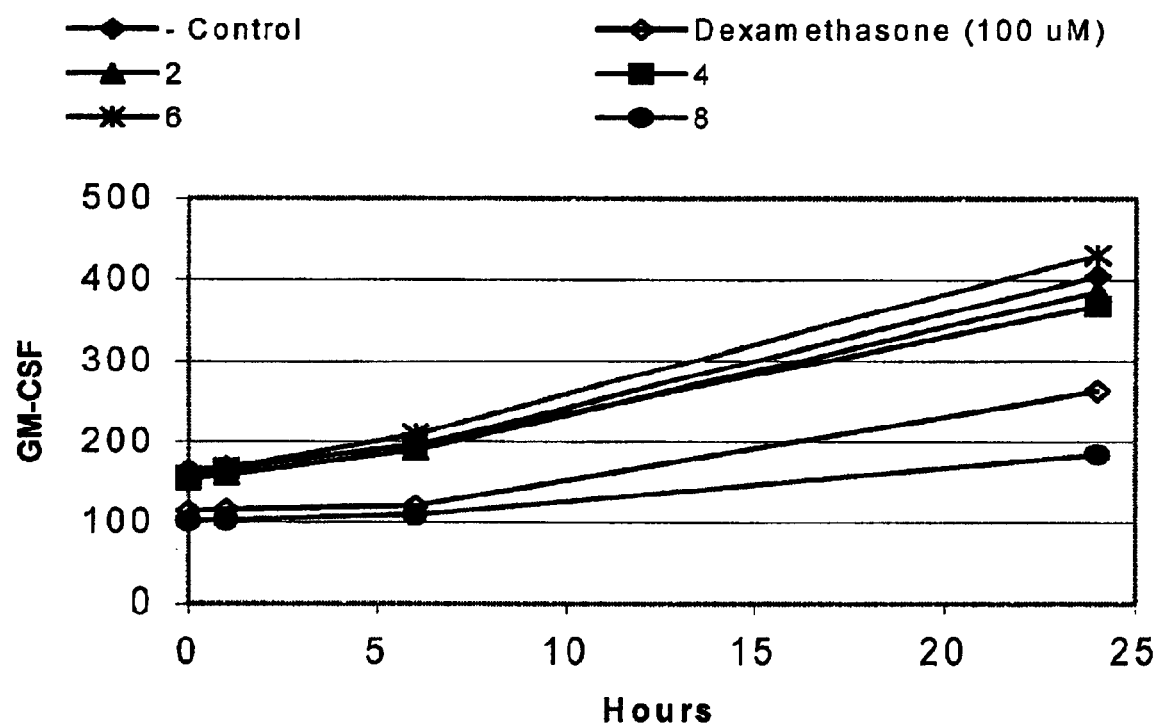

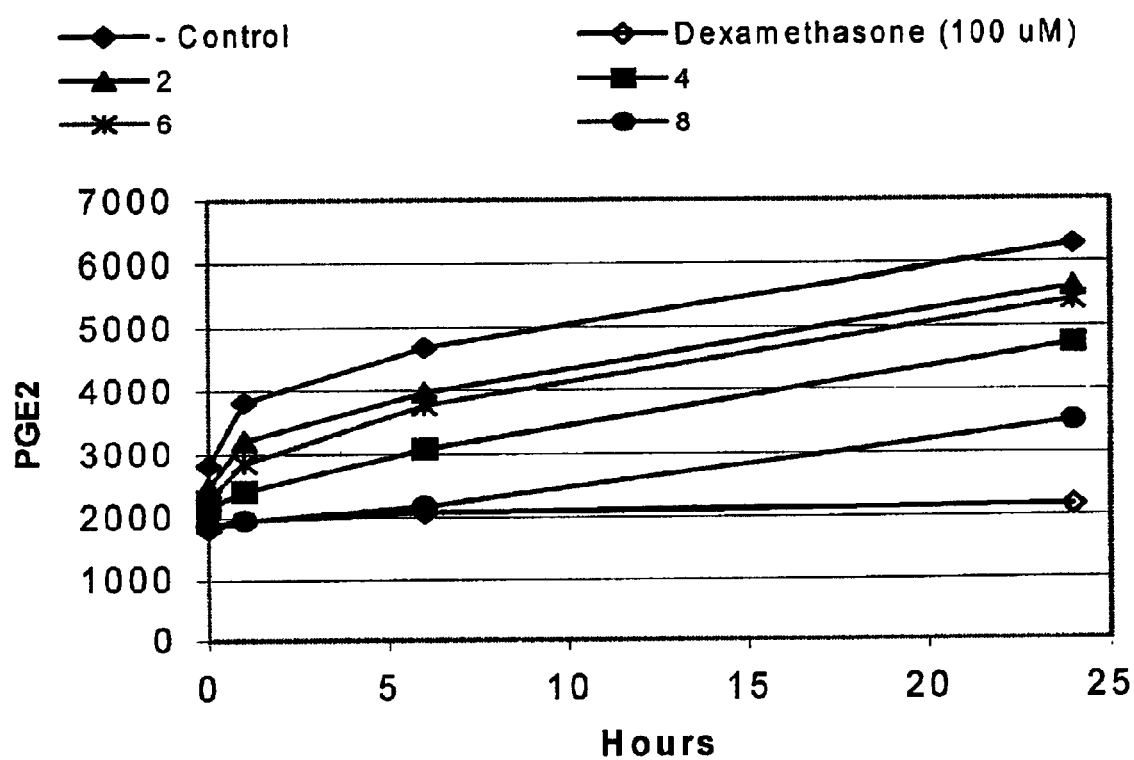

US 6,881,427 B2

TOPICAL ANTI-INFLAMMATORY COMPOSITION CONTAINING LINSEED AND LICORICE EXTRACTS

BACKGROUND

The present invention relates to anti-inflammatory compositions and, more particularly, to topical anti-inflammatory compositions. The compositions of the present invention have particular use as cosmetic and/or dermopharmaceutical compositions.

Human skin is subjected to numerous environmental and other conditions. Some of these environmental conditions, such as sunburn irritate the skin. In addition, the use of skin exfoliants such as the hydroxy acids, as well as other cosmetic compounds used to diminish skin lines and wrinkles, oftentimes irritates the skin. Therefore, it would be useful to provide a topical anti-inflammatory composition to address these and other skin irritants.

One solution has been to use non-steroidal anti-inflammatory drugs, commonly known as NSAIDs. In spite of their widespread use, the therapeutic utility of NSAIDs is offset by a range of side effects, including potentially life-threatening ulcerations and renal toxicity. Topical corticosteroids have also been used as an alternative to the NSAIDS, but such steroidal treatments, particularly when used over long periods, may also lead to a range of serious side effects, including teratogenesis of developing fetal cells.

It would, therefore, be desirable to provide a topical anti-inflammatory composition that would address above and other problems relating to the use of conventional topical anti-inflammatory treatments. It would also be desirable to use naturally occurring ingredients.

SUMMARY

The scope of the present invention is defined solely by the appended claims, and is not affected to any degree by the statements within this summary. By way of introduction, a topical anti-inflammatory composition embodying features of the present invention includes effective amounts of a linseed extract and a licorice extract. Accordingly, the present invention provides a cosmetic or dermopharmaceutical composition for topical use that comprises a pharmaceutically or cosmetically acceptable vehicle for topical treatment and an effective amount of a linseed extract and a licorice extract.

A second topical anti-inflammatory composition embodying features of the present invention includes from about 0.00001 to about 50 percent by weight of a linseed extract and from about 0.00001 to about 50 percent by weight of the composition.

The present invention also includes a method of reducing inflammation that includes topically applying to a site of inflammation an effective amount of a composition that includes a linseed extract and a licorice extract.

Unless otherwise specifically noted, all percentages used in the following specification and claims are by weight. In addition, unless otherwise specifically noted, a weight percentage used in reference to an aqueous solution includes both the solids and liquids present.

BRIEF DESCRIPTION OF THE DRAWINGS

FIG. 2 shows a plot of the amounts of GM-CSF secreted in response to various stimuli.

FIG. 3 shows a plot of the amounts of $PGE_2$ secreted in response to various stimuli.

DETAILED DESCRIPTION OF THE PRESENTLY PREFERRED EMBODIMENTS

Figure 1:
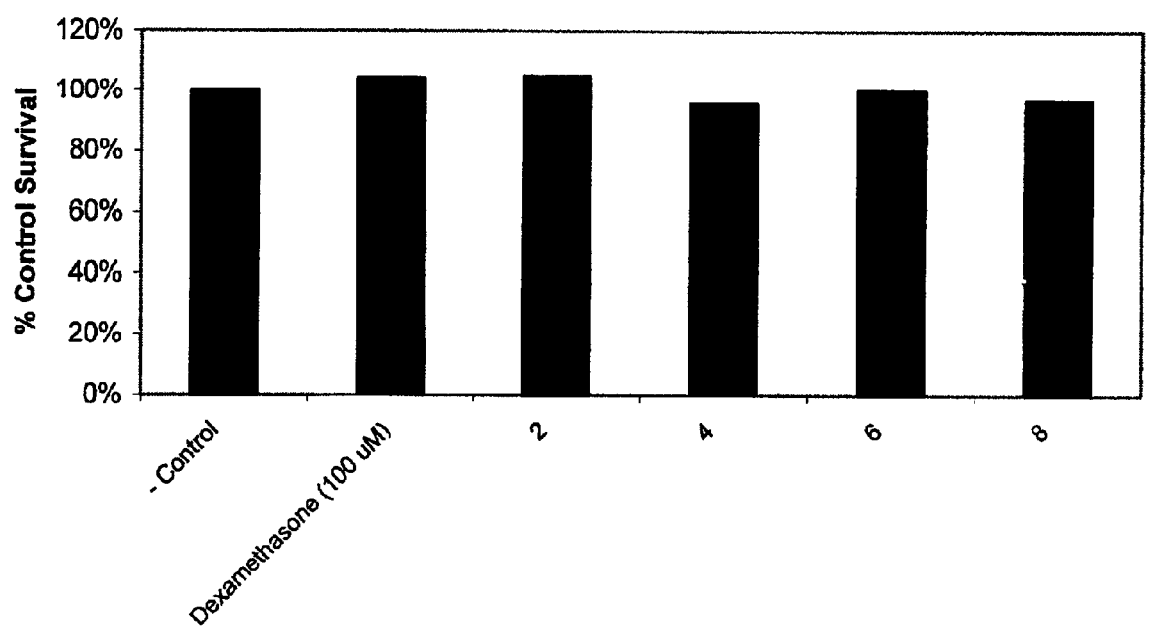
FIG. 1 shows a bar graph indicating toxicities of various materials to TESTSKIN II samples.

A topical anti-inflammatory composition embodying features of the present invention comprises effective amounts of a linseed extract and a licorice extract.

Throughout this description and in the appended claims, the phrase "linseed extract" refers to any compound or combination of compounds obtained from linseed (i.e., "flaxseed," "linum," "*Linum usitatissimum*," or "Linaceae," etc.) and/or from oils obtained from linseed, as well as to chemical derivatives thereof. Representative linseed extracts for use in accordance with the presently preferred embodiments include, but are not limited to, linseed, hydrogenated and unhydrogenated linseed oil, refined linseed oil (e.g., alkali refined linseed oil, acid refined linseed oil, boiled linseed oil, oxidized linseed oil, etc.), linamarin, linatine, linolenic acid and glycerides thereof, linoleic acid and glycerides thereof, oleic acid and glycerides thereof, stearic acid and glycerides thereof, palmitic acid and glycerides thereof, myristic acid and glycerides thereof, and the like, and combinations thereof. Linseed extracts for use in accordance with the presently preferred embodiments can be saturated or unsaturated. A presently preferred linseed extract is the purified fractions of linseed rich in polysaccharides (e.g. β-glucan, uronic acids) and peptidoglycans sold under the trade name SENSILINE by Silab (Cedex, France). The SENSILINE linseed extract is provided in an aqueous solution, and gives a solids analysis of between about 12 and about 20 g/L. In addition, the SENSILINE linseed extract contains proteins in a range of between about 4 and about 7 g/L, a total sugars content in a range of between about 6 and about 9 g/L, and uronic acids in a range less than about 1300 μg/mL.

Preferably, linseed extracts used in accordance with the present invention are present in an amount from about 0.00001% to about 50% by weight of the composition. More preferably, the linseed extract is present in an amount from about 0.00001% to about 40% by weight of the composition. Still more preferably, the linseed extract is present in an amount from about 0.00001 to about 10 percent by weight (i.e., w/w) of the composition, more preferably from about 0.001 to about 6 percent by weight of the composition, and still more preferably from about 0.1 to about 5 percent by weight of the composition. In certain of the presently preferred embodiments, it is desirable that the linseed extract is present in an amount of at least about 1 percent by weight of the composition, more desirably at least about 2 percent by weight of the composition, and still more desirably at least about 3 percent by weight of the composition. The presence of the linseed extract in an amount that is about 4 percent by weight of the composition is particularly preferred at present.

Typically, hydrolyzed linseed extract is provided as an aqueous solution having a solids content of between about 12 and about 20 g/L. Thus, a 4 percent by weight aliquot of the aqueous solution would correspond to about 0.008 percent by weight of "active" linseed extract material.

Throughout this description and in the appended claims, the phrase "licorice extract" refers to any compound or combination of compounds in the glycyrrhiza family (i.e., *Glycyrrhiza glabra*), including glycyrrhiza, glycerrhetic acid (also known as "enoxolone," "uralenic acid," and "glycyrrhetinic acid"), glycyrrhizic acid (also known as "glycyrrhizin," "glycyrrhizinic acid," and "glycyrrhetinic acid glycoside"), derivatives thereof, and combinations thereof. Presently preferred derivatives of licorice extracts include salts (e.g., metal salts, ammonium salts, and the like) and esters (e.g. saturated fatty acid esters, unsaturated fatty acid esters, diacid half esters, glycoside esters, and the like).

Representative saturated fatty acid ester derivatives for use in accordance with the presently preferred embodiments include, but are not limited to, butyrate esters, isovalerate esters, caproate esters, caprylate esters, caprate esters, laurate esters, myristate esters, palmitate esters, stearate esters, arachidate esters, behenate esters, lignocerate esters, cerotate esters, and combinations thereof.

Representative unsaturated fatty acid ester derivatives for use in accordance with the presently preferred embodiments include, but are not limited to, decylenate esters, stillingate esters, dodecylenate esters, palmitoleate esters, oleate esters, ricinoleate esters, petroselinate esters, vaccenate esters, linoleate esters, linolenate esters, eleostearate esters, punicate esters, licanate esters, parinarate esters, gadoleate esters, arachidonate esters, eicosenate esters, docosenate esters, cetoleate esters, erucate esters, docosadienate esters, selacholeate esters, and combinations thereof.

Representative diacid half ester derivatives for use in accordance with the presently preferred embodiments (i.e., derivatives of licorice extracts comprising an ester linkage between the licorice extract and one of the two carboxylic acid moieties of a diacid, preferably an $\alpha,\omega$-diacid) include, but are not limited to, succinate half esters, glutarate half esters, adipate half esters, pimelate half esters, suberate half esters, azelate half esters, and combinations thereof.

Preferred licorice extract ester derivatives include saturated and unsaturated esters of glycerrhetic acid and glycyrrhizic acid in which the ester portion of the molecule contains from 2 to 24 carbon atoms, more preferably from 10 to 24 carbon atoms, still more preferably from 16 to 24 carbon atoms. Representative licorice extract ester derivatives for use in accordance with the present invention include but are not limited to monoammonium glycyrrhizinate, monopotassium glycyrrhizinate, dipotassium glycyrrhizinate, 1-beta-glycyrrhetic acid, stearyl glycyrrhetinate, 3-stearyloxy-glycyrrhetinic acid, disodium 3-succinyloxy-beta-glycyrrhetinate, and the like. Stearyl glycyrrhetinate is a preferred licorice extract, and the stearyl glycyrrhetinate sold under the tradename NET-STG by Barnet Products Corporation (Englewood Cliffs, N.J.) is especially preferred.

Preferably, licorice extracts used in accordance with the present invention are present in an amount from about 0.00001% to about 50% by weight of the composition. More preferably, the licorice extract is present in an amount from about 0.00001% to about 40% by weight of the composition. Still more preferably, the licorice extracts is present in an amount from about 0.00001 to about 3 percent by weight (i.e., w/w) of the composition, more preferably from about 0.0001 to about 2 percent by weight of the composition, and still more preferably from about 0.001 to about 1.5 percent by weight of the composition.

In certain of the presently preferred embodiments, it is desirable that the licorice extract is present in an amount of at least about 0.01 percent by weight of the composition, more desirably at least about 0.03 percent by weight of the composition, and still more desirably at least about 0.05 percent by weight of the composition. The presence of the licorice extract in an amount of about 0.1 percent by weight of the composition is particularly preferred at present.

Compositions embodying features of the present invention are effective in lowering background levels of both $PGE_2$ (Prostaglandin $E_2$), a biomarker of irritant-induced inflammation, and GM-CSF (Granulocyte-Macrophage Colony Stimulating Factor), a biomarker of immuno-induced inflammation. The efficacy of these compositions is similar to that of dexamethasone, a synthetic glucocorticoid that has long been used therapeutically as an immunosuppressive and as an anti-inflammatory agent. Without wishing to be bound to a particular theory or to in any way diminish the scope of the appended claims and their equivalents, it is presently believed that the mechanism of action of compositions embodying features of the present invention may involve a novel transcription regulatory effect exerted by the combination of linseed extract and licorice extract acting together to modulate inflammatory response. Indeed, it has been found, surprisingly and unexpectedly, that the combination of the linseed extract and the licorice extract exerts a synergistic effect on the lowering of background levels of $PGE_2$ and GM-CSF.

In one embodiment of the present invention, one or more bioflavonoids may be added to the composition to provide additive benefit in lowering irritant phorbol myristate acetate (PMA)-induced cellular response. Preferred bioflavonoids include but are not limited to multi-source citrus bioflavonoids, bitter orange flower bioflavonoids, and fatty acid-modified hesperetin laurate bioflavonoids.

To prepare the compositions according to the present invention, the linseed extract and the licorice extract are mixed with a pharmaceutically or cosmetically acceptable vehicle or carrier. The cosmetically acceptable vehicle acts as a dilutant, dispersant or carrier for other materials present in the composition, so as to facilitate their distribution when the composition is applied to the skin. Vehicles other than water can include liquid or solid emollients, solvents, humectants, thickeners and powders. Other suitable vehicles are described in U.S. Pat. No. 6,184,247, the entire contents of which are incorporated herein by reference.

The pharmaceutically or cosmetically acceptable vehicle will usually form from about 10% to about 99.9%, preferably from about 50% to 99% by weight of the total composition, and can, in the absence of other cosmetic adjuncts or additives, form the balance of the composition.

The compositions of the present invention may be formulated as a solution, gel, lotion, cream, ointment, oil-in-water emulsion, water-in-oil emulsion, stick, spray, ointment, paste, mousse, suppository, and the like or other pharmaceutically acceptable form. In addition, the compositions can be transferred to a site of inflammation from the gauze portion of an adhesive bandage, for example of the type sold under the tradename BAND-AID by Johnson & Johnson (Skillman, N.J.).

The compositions of the present invention may also contain various known and conventional cosmetic ingredients so long as they do not detrimentally affect the desired anti-inflammatory effect provided by the combination of the linseed extract and licorice extract. For example, the composition of the present invention can further include one or more additives or other optional ingredients well known in the art, which can include but are not limited to fillers (e.g., solid, semi-solid, liquid, etc.); carriers; diluents; emollients; emulsifiers; surfactants; structuring agents; thickening agents; gelling agents; vitamins, retinoids, and retinols (e.g., vitamin $B_3$, vitamin A, etc.); pigments; fragrances; sunscreens and sunblocks; anti-oxidants and radical scavengers; organic hydroxy acids; desquamation agents; exfoliants;

skin lightening agents; skin conditioners; moisturizers; ceramides, pseudoceramides, phospholipids, sphingolipids, cholesterol, hyaluronic acid and its derivatives, collagen synthesis promoters, glucosamine, pharmaceutically acceptable penetrating agents (e.g., n-decylmethyl sulfoxide, lecithin organogels, etc.); preservatives; antimicrobial agents; and the like; and combinations thereof. Other suitable additives and/or adjuncts are described in U.S. Pat. No. 6,184,247, the entire contents of which are incorporated herein by reference.

Methods of reducing inflammation embodying features of the present invention include applying topically to a site of inflammation an effective amount of a composition of a type described herein, which includes a linseed extract and a licorice extract. The frequency at which topical applications in accordance with the present invention are performed is not limited, and may vary depending on the type and severity of inflammation to be treated. In addition, the type and cause of inflammation to be treated by topically applying compositions embodying features of the present invention is not limited, and includes all types and causes of inflammation having a potential to benefit from contact with a composition in accordance with the present invention.

The following examples developed for a composition containing a linseed extract and stearyl glycyrrhetinate, are provided solely by way of illustration, and are not intended to limit the scope of the appended claims or their equivalents.

EXAMPLES

The anti-inflammatory potential of a composition according to the present invention that includes a combination of linseed extract and licorice extract was evaluated as described herein. The release of PGE2 and GM-CSF from skin tissue provides a measure of protective potential following pre-incubation with test materials, whereas the reduction of MTT (3-[4,5-dimethylthiazol-2yl]-2,5-diphenyl-2H-tetrazolium bromide) provides an estimate of toxicity potential.

The skin tissue used in this study, TESTSKIN II (Organogenesis Inc., Canton, Mass.), is constructed from human skin with anatomical structures and physiological functions that simulate actual living skin. This tissue has an upper epidermal layer with well-differentiated keratinocytes and stratum corneum and a lower dermal layer with living fibroblasts able to produce collagen matrix.

The compositions of the test materials of this study are summarized in Table 1 below. The test materials identified in Table 1 include a blank cream (test material 2), a cream containing stearyl glycyrrhetinate (test material 4), a cream containing linseed extract (test material 6), a cream containing a combination of stearyl glycyrrhetinate and linseed extract (test material 8), a positive control (dexamethasone), and a negative control (no treatment)

TABLE 1

| Ingredient | Test Material 2 % | Test Material 4 % | Test Material 6 % | Test Material 8 % |
|---|---|---|---|---|
| Deionized Water | 56.919 | 56.819 | 52.919 | 52.819 |
| Glycerin | 0.500 | 0.500 | 0.500 | 0.500 |
| Glyceryl Polymethacrylate | 15.000 | 15.000 | 15.000 | 15.000 |
| Polysorbate 20 | 0.500 | 0.500 | 0.500 | 0.500 |
| Squalene | 10.000 | 10.000 | 10.000 | 10.000 |
| Sorbitan Stearate | 3.000 | 3.000 | 3.000 | 3.000 |
| L-Arginine | 5.000 | 5.000 | 5.000 | 5.000 |
| Butylene Glycol | 4.900 | 4.900 | 4.900 | 4.900 |
| Stearyl Glycyrrhetinate (Barnet) | | 0.100 | | 0.100 |
| Hydrolyzed Linum Usitatissimum (Linseed) Extract (Silab) | | | 4.000 | 4.000 |
| Other Additives | 4.181 | 4.181 | 4.181 | 4.181 |

The test materials were evaluated for exposure periods of 4, 8, and 24 hours, and their toxicity was evaluated for an exposure period of 24 hours. Test materials 2, 4, 6, and 8 were used neat. The positive control (i.e., dexamethasone) was used in a concentration of 100 $\mu$M. All dilutions were made in growth media, and assays were performed in triplicate.

Six-well Falcon plates are available from Becton Dickinson & Company (Bedford, Mass.). Millicell transwell inserts and dosing pads are available from Millipore Corporation (Bedford, Mass.). The growth medium, DMEM/F12, is available from Life Technologies, a division of Invitrogen Corporation (Carlsbad, Calif.). A high sensitivity colorimetric competitive ELISA immunoassay kit against $PGE_2$, and a quantikine colorimetric sandwich ELISA immunoassay kit against human GM-CSF (R&D DE2100 and R&D DGM00, respectively) are available from R&D Systems, Inc. (Minneapolis, Minn.,). MTT (e.g., M2128) is available from Sigma-Aldrich (Milwaukee, Wis.). The assay methods used in this example are described in numerous references including: *J. Imm. Methods,* 1983, by Mosman; *Biochem. Pharm.,* 1976, by R. J. Flower and G. J. Blackwell; *Proc. Natl. Acad. Sci. USA,* 1988, by J. Raud et al.; *J. Immunol.,* 1985, by J. G. Giri et al.; *Science,* 1974, by M. B. Taubman et al.; *Med. Pharm.,* 1990, by S. Haga et al.; *J. Cell Physiol.,* 1990, by A. F. Lopez et al.; and *Nature,* 1989, by F. Bussolino et al.

All supplies and handling equipment are sterilized, and techniques for maintaining sterility are used. Skin tissue is punched out using an 8 mm biopsy punch from the middle section and transferred to a well of a six-well plate containing transwell inserts and 1 mL of growth media. Tissues are transferred to a humidified 37° C. incubator supplied with 10% $CO_2$ and incubated overnight.

Test materials to be used are dosed on a sterile dosing pad (10 $\mu$L/pad) and placed on top of tissue. Dosed tissues are returned to the incubator and incubated for a specified amount of time (e.g., 4 hours), after which the supernatants are replaced with fresh media. Collected supernatants are used for $PGE_2$ and GM-CSF assays.

$PGE_2$ Detection

Quantification of $PGE_2$ in the supernatant at a specified point in time is carried out according to protocols suggested by the supplier. For example, 100 $\mu$l of samples or standards (recombinant $PGE_2$ at 50 $\mu$g/mL serially diluted to 1000, 500, 250, 125, 62.5, 31.2, 15.6, and 7.8 pg/mL in assay buffer ED1) are added to appropriate wells coated with anti-mouse antibodies. Four controls are included: total activity, non-specific binding, maximum binding, and substrate blank. The total activity control contains only directly added $PGE_2$ HS conjugate. The non-specific binding control contains $PGE_2$ HS conjugate in buffer in place of samples or standards but lacks anti $PGE_2$ HS antibody. The maximum binding control contains both $PGE_2$ HS conjugate and anti $PGE_2$ HS antibody but contains buffer in place of sample or standard. The substrate blank control contains only buffer solution. After 50 µL of $PGE_2$ HS conjugate solution and 50 µL of $PGE_2$ HS antibody solution are added to the sample, standard, and appropriate control wells, the plate is incubated at 4–8° C. for 18 hours. After incubation, solution is aspirated from the wells, which are washed 3 times in wash buffer. Substrate (pNPP in buffer, 200 µL) is added to each well and the plate is incubated at 37° C. for 1 hour. Following incubation, 50 µL of stop solution (trisodium phosphate solution) is added and the optical density is measured immediately at 405 nm (reference wavelength of 570–590 nm) using a microplate spectrophotometer. The amount of $PGE_2$ present in the supernatant is determined by comparison to the calibration curve generated by the recombinant $PGE_2$ standard.

GM-CSF Detection

Quantification of GM-CSF in the supernatant at a specified point in time is carried out according to protocols suggested by the supplier. For example, 100 µL of samples (culture supernatant) or standards (recombinant GM-CSF at 500 pg/mL serially diluted to 250, 125, 62.5, 31.2, 15.6, and 7.8 pg/mL in sample diluent) are added to appropriate wells coated with anti-GM-CSF antibodies. The plate is incubated at room temperature for 2 hours. Following incubation, samples are removed from the wells and the wells are washed 4 times with wash buffer. Anti-GM-CSF conjugates (200 µL) are added to each well and the plate is incubated at room temperature for 1 hour. Samples are again removed following incubation and the wells are washed 4 times as before. After the final wash, 200 µL of substrate solution is added to each well and the plate is incubated at room temperature for 20 minutes. A stop solution (1N sulfuric acid, 50 µL) is added and the optical density is obtained at 450 nm (reference 540/570 nm). The amount of GM-CSF present in the supernatant is determined from a calibration curve generated by the recombinant GM-CSF standard.

MTT

Tissues free of test materials are incubated with 2 mg/mL of MTT solution (made up in growth media) in a humidified 37° C. incubator supplied with 10% $CO_2$ for 2 hours. After 2 hours of incubation, MTT solution is removed and the tissues are washed with PBS. The Formazan salt formed is eluted by incubation with 4 mL of isopropanol for 1 hour. Spent MTT solution is read in a 96 well flat bottom plate at $A_{540}$.

Table 2 below shows MTT data for cells treated with various test materials over 24 hour exposure periods. Assays are performed in triplicate, and the numbers shown correspond to averages of the triplicate treatments.

TABLE 2

| Stimulus | Test Material | % Survival ± SD |
|---|---|---|
| None | 2 | 105 ± 10 |
|  | 4 | 96 ± 6 |
|  | 6 | 100 ± 11 |
|  | 8 | 97 ± 2 |
|  | dexamethasone | 104 ± 11 |

FIG. 1 shows a bar graph of toxicities of various materials over a 24-hour exposure period for TESTSKIN II samples. Toxicity is assayed after the exposure period by means of MTT reduction.

As shown by the data in Table 2 and FIG. 1, none of the test materials appears to be adversely toxic based on % survival following treatment. PMA (10 ng/mL), which is used as a positive control of contact irritation, is mildly toxic to TESTSKIN II tissue, albeit to a statistically insignificant degree (criteria set at $p \leq 0.01$).

Table 3 below shows data corresponding to IL-1α, $PGE_2$ and GM-CSF secretion in cells treated with various test materials over 24 hour exposure periods. Assays are performed in triplicate, and the numbers shown correspond to averages of the triplicate treatments.

TABLE 3

| TEST MATERIAL | 0 Hr | 4 Hr | 8 Hr | 24 Hr |
|---|---|---|---|---|
| IL-1α | | | | |
| 2 | 22.00 ± 9.69 | 27.80 ± 4.38 | 29.37 ± 2.83 | 32.66 ± 2.27 |
| 4 | 22.00 ± 9.69 | 31.83 ± 14.02 | 34.29 ± 14.80 | 42.96 ± 12.97 |
| 6 | 22.00 ± 9.69 | 32.02 ± 15.35 | 34.54 ± 16.14 | 43.95 ± 12.10 |
| 8 | 22.00 ± 9.69 | 25.56 ± 10.31 | 26.18 ± 10.27 | 40.46 ± 14.37 |
| Negative Control | 22.00 ± 9.69 | 26.16 ± 10.33 | 27.18 ± 10.40 | 32.47 ± 10.94 |
| Dexamethasone | 22.00 ± 9.69 | 23.35 ± 10.39 | 24.45 ± 9.47 | 25.42 ± 8.94 |
| $PGE_2$ | | | | |
| 2 | 1420 ± 169 | 2453 ± 92 | 3398 ± 137 | 5836 ± 377 |
| 4 | 1420 ± 169 | 2159 ± 220 | 2572 ± 236 | 4911 ± 409 |
| 6 | 1420 ± 169 | 2264 ± 144 | 3190 ± 159 | 5758 ± 145 |
| 8 | 1420 ± 169 | 1874 ± 145 | 2012 ± 159 | 3555 ± 278 |
| Negative Control | 1420 ± 169 | 2816 ± 92 | 4219 ± 382 | 6693 ± 171 |
| Dexamethasone | 1420 ± 169 | 1964 ± 444 | 2077 ± 487 | 2161 ± 564 |

TABLE 3-continued

| TEST MATERIAL | 0 Hr | 4 Hr | 8 Hr | 24 Hr |
|---|---|---|---|---|
| | | GM-CSF | | |
| 2 | 92.61 ± 5.64 | 153.40 ± 6.42 | 176.26 ± 6.87 | 390.34 ± 15.89 |
| 4 | 92.61 ± 5.64 | 155.55 ± 5.25 | 181.21 ± 9.99 | 374.39 ± 14.97 |
| 6 | 92.61 ± 5.64 | 156.18 ± 14.87 | 186.36 ± 9.62 | 437.31 ± 40.48 |
| 8 | 92.61 ± 5.64 | 101.54 ± 6.16 | 105.22 ± 6.48 | 182.86 ± 9.09 |
| Negative Control | 92.61 ± 5.64 | 147.76 ± 6.17 | 166.04 ± 6.87 | 394.30 ± 15.89 |
| Dexamethasone | 92.61 ± 5.64 | 116.00 ± 5.64 | 120.40 ± 552 | 262.03 ± 35.82 |

FIGS. 2 and 3, respectively, show plots of the amounts of GM-CSF and PGE$_2$ secreted after exposure to various test materials. Tissues are pre-incubated with test materials for 4 hours prior to being stimulated by PMA or Histamine. Secreted IL-1α, PGE$_2$ and GM-CSF are measured using the ELISA method. Although the cytokines PGE$_2$ and GM-CSF shown in Table 3 and in FIGS. 2–3 are used as indicators of irritancy, inflammation and immunostimulation, it should be noted that the TESTSKIN II skin model is devoid of immune cells such as APC (antigen presenting cells).

As shown by FIG. 2, the cream containing both stearyl glycyrrhetinate and linseed extract (test material 8) successfully lowers the amount of GM-CSF secreted below the level achieved using dexamethasone, and well below the levels achieved using creams containing the individual ingredients, stearyl glycyrrhetinate and linseed extract, by themselves (test materials 4 and 6, respectively).

Similarly, as shown by FIG. 3, the cream containing both stearyl glycyrrhetinate and linseed extract (test material 8) successfully lowers the amount of PGE$_2$ secreted well below the levels achieved using creams containing the individual ingredients, stearyl glycyrrhetinate and linseed extract, by themselves (test materials 4 and 6, respectively). Accordingly, it is evident that the combination of the linseed extract and the licorice extract exerts a surprising and unexpected synergistic effect on the lowering of background levels of PGE$_2$ and GM-CSF.

Upon exposure to the test materials and in the absence of additional stimulation, no significant secretion of IL-1α, PGE$_2$ and GM-CSF is triggered beyond the level of background (i.e., negative control). However, the sample containing stearyl glycyrrhetinate and linseed extract (8) decreases the background level of PGE$_2$ and GM-CSF after 24 hours with no additional stimulation.

Although stimulation by PMA fails to induce PGE$_2$ secretion above the background level after 24 hours of exposure, the background level of PGE$_2$ secretion is suppressed when tissues are pretreated with test material 8 or dexamethasone prior to PMA exposure. In addition, test material 8 provides some protection against Histamine induced GM-CSF secretion when tissues are challenged with exogenous Histamine.

Eye cream containing SENSILINE linseed extract, NETSTG stearyl glycyrrhetinate, or a combination of the two is found to be non-toxic (based on MTT cell survival data) and non-irritating (based on IL-1α, PGE$_2$ and GM-CSF secretion data) to the skin model in this study. Eye creams containing a combination of the two active ingredients provide a measure of protection against inflammatory/irritation response upon exogenous stimulation with PMA (non-sensitizing irritant) or Histamine (Type IV hypersensitivity-like response). It is noted that the combined presence of the two active ingredients acts synergistically in lowering background levels of PGE$_2$ and GM-CSF to levels observed for dexamethasone.

The foregoing detailed description and examples have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A topical composition comprising an anti-inflammatory composition consisting essentially of a linseed extract and a licorice extract, wherein the linseed extract comprises from about 0.1 to about 5 percent by weight of the topical composition and wherein the licorice extract comprises from about 0.001 to about 1.5 percent by weight of the topical composition.

2. The topical composition of claim 1 wherein the licorice extract is selected from the group consisting of glycyrrhiza, glycerrhetic acid, glycyrrhizic acid, derivatives thereof, and combinations thereof.

3. The topical composition of claim 2 wherein the derivatives are selected from the group consisting of salts, esters, and a combination thereof.

4. The topical composition of claim 3 wherein the salts are selected from the group consisting of metal salts and ammonium salts.

5. The topical composition of claim 3 wherein the esters are selected from the group consisting of fatty acid esters, diacid half esters, and glycoside esters.

6. The topical composition of claim 5 wherein the fatty acid esters are selected from the group consisting of saturated fatty acids esters and unsaturated fatty acid esters.

7. The topical composition of claim 6 wherein the licorice extract is stearyl glycyrrhetinate.

8. The topical composition of claim 1 wherein the linseed extract comprises about 4 percent by weight of the topical composition.

9. The topical composition of claim 7 wherein the stearyl glycyrrhetinate comprises about 0.1 percent by weight of the topical composition.

10. The topical composition of claim 1 further comprising at least one bioflavonoid.

11. A method of reducing inflammation comprising applying topically to a site of inflammation the topical composition of claim 1.

12. The method of claim 11 wherein the licorice extract is selected from the group consisting of glycyrrhiza, glycerrhetic acid, glycyrrhizic acid, derivatives thereof, and combinations thereof.

13. The method of claim 12 wherein the licorice extract is stearyl glycyrrhetinate.

* * * * *